United States Patent [19]

Ray

[11] 4,119,638

[45] Oct. 10, 1978

[54] THIO-ESTER OF 1 (P-CHLOROBENZOYL)-5-METHOXY-2-METHYLINDOLE-3-ACETIC ACID

[75] Inventor: Richard E. Ray, Morton Grove, Ill.

[73] Assignee: G. D. Searle & Co., Chicago, Ill.

[21] Appl. No.: 745,745

[22] Filed: Nov. 29, 1976

[51] Int. Cl.$^2$ .............................................. C07D 209/04
[52] U.S. Cl. ............................. 260/326.12 A; 424/274
[58] Field of Search .............. 260/326.12 R, 326.12 A

[56] References Cited

U.S. PATENT DOCUMENTS

| 3,161,654 | 12/1964 | Shen | 260/326.12 A |
| 3,522,272 | 7/1970 | Chemerda et al. | 260/326.12 A |
| 3,691,199 | 9/1972 | Kobaysahi et al. | 260/326.12 R |
| 3,894,044 | 7/1975 | Sturm et al. | 260/326.12 R |

OTHER PUBLICATIONS

Chem. Abstracts, 1947–1956–Subject Index, 6568s–6569s.
Chem. Abstracts, 50:2543h.

*Primary Examiner*—Ethel G. Love
*Attorney, Agent, or Firm*—Joy A. Serauskas

[57] ABSTRACT

This invention relates to a new class of compounds of the indole series. Particularly, it relates to novel thio esters of 1-(p-chlorobenzoyl)-5-methoxy-2-methylindole-3-acetic acid. These novel compounds are prepared by reacting 1-(p-chlorobenzoyl)-5-methoxy-2-methylindole-3-acetic acid with an appropriate thiol and diethyl phosphorocyanidate or diphenyl phosphorazidate in the presence of triethylamine in a dimethylformamide solution. These compounds are useful anti-inflammatory agents.

14 Claims, No Drawings

THIO-ESTER OF 1 (P-CHLOROBENZOYL)-5-METHOXY-2-METHYLINDOLE-3-ACETIC ACID

This invention relates to a new class of compounds of the indole series. Particularly, it relates to novel thio esters of 1-(p-chlorobenzoyl)-5-methoxy-2-methylindole-3-acetic acid having the following structural formula

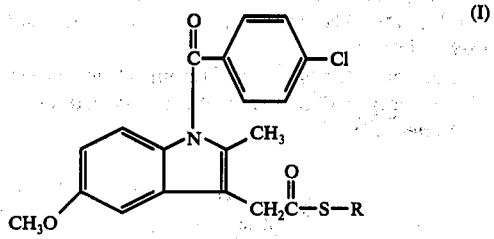

wherein R represents: linear or branched chain alkyl radical containing 1 to 9 carbon atoms which can be optionally substituted by one or more phenyl radicals; a cycloalkyl radical containing 3 to 6 carbon atoms which can be optionally substituted by an alkyl radical containing 1 to 9 carbon atoms or halo; phenyl, benzyl, monosubstituted or polysubstituted phenyl wherein the substituent can be linear or branched chain alkyl radical containing 1 to 9 carbon atoms, halo, alkoxy wherein the alkyl radical contains 1 to 9 carbon atoms, amino, or nitro and may be alike or different.

The linear or branched chain alkyl radicals containing 1 to 9 carbon atoms which are encompassed by formula I are exemplified by methyl, ethyl, propyl, butyl, pentyl, hexyl, heptyl, octyl, nonyl and the corresponding branched chain isomers thereof. The cycloalkyl radicals containing 3 to 6 carbon atoms are exemplified by cyclopropyl, cyclobutyl, cyclopentyl and cyclohexyl. The halo atoms are exemplified by fluoro, chloro, bromo, and iodo. The alkoxy radicals are exemplified by methoxy, ethoxy, propoxy, butoxy, pentoxy, hexoxy, hepoxy, octoxy and nonoxy.

The point of attachment of the alkyl, halo, alkoxy, amino or nitro substituent in the monosubstituted phenyl radical is not critical. Thus, the substituent may be in an ortho, meta or para position.

Preferred embodiments of the present invention as set out in formula I are those embodiments in which R can be 1-methylpropyl or 2-methylpropyl. Specifically S-1-methyl-1-propyl 1-(4-chlorobenzoyl)-5-methoxy-2-methyl-3-indolethioacetate and S-2-methyl-1-propyl 1-(4-chlorobenzoyl)-5-methoxy-2-methyl-3-indolethioacetate.

Preferred embodiments of the present invention as set out in formula I are those embodiments in which R can be cyclohexyl. Specifically S-cyclohexyl 1-(4-chlorobenzoyl)-5-methoxy-2-methyl-3-indolethioacetate.

Preferred embodiments of the present invention as set out in formula I are those embodiments in which R can be phenyl, benzyl, 4-tert-butylphenyl, 2,4,6-trimethylphenyl, 4-aminophenyl, 4-chlorophenyl, 4-methoxyphenyl, 4-methylphenyl, 4-nitrophenyl,2,5 dichlorophenyl and 3,4-dichlorophenyl. Specifically, S-phenyl 1-(4-chlorobenzoyl)-5-methoxy-2-methyl-3-indolethioacetate, S-phenylmethyl 1-(4-chlorobenzoyl)-5-methoxy-2-methyl-3-indolethioacetate, S-4-tertbutylphenyl 1-(4-chlorobenzoyl)-5-methoxy-2-methyl-3-indolethioacetate, S-2,4,6-trimethylphenyl 1-(4-chlorobenzoyl)-5-methoxy-2-methyl-3-indolethioacetate, S-4-aminophenyl 1-(4-chlorobenzoyl)-5-methoxy-2-methyl-3-indolethioacetate, S-4-chlorophenyl 1-(4-chlorobenzoyl)-5-methoxy-2-methyl-3-indolethioacetate, S-4-methoxyphenyl 1-(4-chlorobenzoyl)-5-methoxy-2-methyl-3-indolethioacetate, S-3,4-dichlorophenyl 1-(4-chlorobenzoyl)-5-methoxy-2-methyl-3-indolethioacetate, S-4-nitrophenyl 1-(4-chlorobenzoyl)-5-methoxy-2-methyl-3-indolethioacetate, S-4-methylphenyl 1-(4-chlorobenzoyl)-5-methoxy-2-methyl-3-indolethioacetate, S-2,5-dichlorophenyl 1-(4-chlorobenzoyl)-5-methoxy-2-methyl-3-indolethioacetate.

The compounds to which this invention relates are useful by reason of their valuable biological properties. As especially valuable property characteristic of the instant compounds is their anti-inflammatory activity.

The anti-inflammatory utility of the instant compounds is evidenced by the results of a standardized assay for their capacity to inhibit the edema induced in rats by injection of *Mycobacterium butyricum*. The procedure which is similar to one described by Pearson et al. in *Arthritis Rheumat.*, 2, 440 (1959) follows.

CHRONIC POLYARTHRITIC ASSAY

Male, albino, CrL: COBS ® CD ® (SD) BR strain rats (60–70 grams) obtained from Charles River Breeding Laboratories, Inc. in Wilmington, Massachusetts are injected subcutaneously in the plantar region of each hind foot with 0.05 ml. of an adjuvant containing 5 mg. of heat killed and dried *Mycobacterium butyricum* per ml. of paraffin oil. The compound is suspended in phosphate buffered saline and administered daily intragastrically at doses ranging from 0.2 to 300 mg/kg for a period of 19 days beginning on the day of inoculation. A control group treated with vehicle only was included. Indomethacin suspended in phosphate buffered saline and administered daily intragastrically at doses ranging from 0.2 to 1.0 mg. kg. was employed as the reference standard. Each daily dose of compound was administered in two separate aliquots, one administered between 8:00 A.M.–9:00 A.M. and the other between 3:00 P.M.–4:00 P.M. On day 20 post inoculation the volume displacement of the hind limbs was measured on a mercury plethysmograph (UGO BASILLE). Doses of compounds are considered to be active if they produce a significant decrease in volume displacement of the hind limbs as compared to controls by Wilcoxon Rank Sum Test.

A representative compound of this invention which is particularly active in the above-mentioned assay is S-4-tertbutylphenyl 1-(4-chlorobenzoyl)-5-methoxy-2-methyl-3-indolethioacetate.

Still further evidence of the anti-inflammatory utility of the instant compounds is provided by the following assay which is similar to one described by Pearson et al. in Arthritis Rheumat., 2, 440 (1959). Intact male Charles River rats are randomized in groups of 12, one group for each compound to be tested plus one group to serve as controls. Each animal is injected subcutaneously (without any anesthesia) in the plantar region of each foot with 0.25 mg. of dry heat-killed *Mycobacterium butyricum* (Difco 0460-33) suspended in 0.05 ml. of incomplete Freund's adjuvant whereupon the prescribed dose of compound, suspended in phosphate-buffered saline, is intragastrically administered. Administration thus of compound is repeated daily for the next 18 consecutive days, the initial dose being 30 mg/kg/day intragastrically. The control group is identically and concurrently administered vehicle alone. On the 20th day, the rats are sacrificed and the total volume of each pair of hind feet is measured in arbitrary units. A compound is considered anti-inflammatory if the average volume (T) of the hind feet in the group treated therewith is significantly ($P \leq 0.05$) less than the corresponding value (C) for the control group. Indomethacin administered intragastrically has an $ED_{50}$ of approximately 0.2 mg/kg/day in this test.

The therapeutic treatment of inflammatory diseases with anti-inflammatory agents may induce gastrointestinal side effects and intolerance. Gastric mucosal damage of varying degrees have been observed in laboratory animals receiving these type of compounds. A good correlation regarding mucosal damage exists between findings in laboratory animals and humans. It has been found that the compounds of the present invention display little or no gastrointestinal side-effects as is evidenced by the following studies.

GASTRIC ULCERATION STUDY

Adult male Charles River rats [Crl: COBS, CD (SD) BR] weighing 200 to 230 g and in groups ranging from 6-12 animals per dose were used. The animals were housed in individual wire mesh cages to prevent coprophagy. The rats were fasted 24 hours prior to the test but allowed to drink water ad libitum. Fasting was continued during the three day test procedure. On test days 1 and 2, suspensions of the test compounds were administered intragastrically in 0.5% methylcellulose twice daily (9:00 a.m. and 3:00 p.m.) employing a volume of 10.0 ml/kg while the control animals received only the vehicle. On test day 3, all rats were sacrificed, observed for gross pathology, and the stomachs were carefully removed intact. The stomachs were then cut open along the greater curvature, gently rinsed with tap water and examined for the presence of ulcers in the glandular region using a 10 X power stereomicroscope. An ulcer is defined as an erosion involving any segment of the gastric submucosa irrespective of the extent of penetration. The number of ulcers occuring in each stomach is counted. The incidence of ulceration in each test group was also recorded.

INTESTINAL ULCERATION STUDY

Groups of 6 to 22 non-fasted adult male Charles River rats [Crl:COBS CD (SD) BR] weighing 180 to 220 g were individually housed. Food and water were provided ad libitum throughout the study. The test compounds were administered once intrasgastrically on the first day of the test employing a 0.5% methylcellulose suspension at a volume of 10 ml/kg. Three days after administration of the test compounds, the animals were sacrificed, posted and the abdominal activity was grossly inspected for the presence or absence of intestinal adhesion and or perforation (1).

The intragastric administration of a representative compound of this invention e.g. S-4-tertbutylphenyl 1-(4-chlorobenzoyl)-5-methoxy-2-methyl-3-indolethioacetate at doses ranging 10 to 100 mg/kg did not produce any gastric ulcerations in fasted rats. Only one out of twelve animals showed minor irritation at the 300 mg/kg dose of S-4-tertbutylphenyl 1-(4-chlorobenzoyl)-5-methoxy-2-methyl-3-indolethioacetate. In contrast, the reference standard anti-inflammatory agents produce dose-dependent ulcerations with a median ulcerogenic dose ranging from 2 to 9.9 mg/kg, i.g.

The intragastic administration of S-4-tertbutylphenyl 1-(4-chlorobenzoyl)-5-methoxy-2-methyl-3-indolethioacetate at the highest tested dose of 400 mg/kg did not produce intestinal lesions or adhesions. A possible abdominal extravascular bleeding was noted in one of six animals in each of the 300 and 400 mg/kg test groups. On the other hand, indomethacin produced marked intestinal adhesions at doses ranging from 10 to 40 mg/kg, i.g. Also, some deaths were seen with indomethacin.

The compounds of the present invention are conveniently prepared according to the procedure illustrated by Scheme A

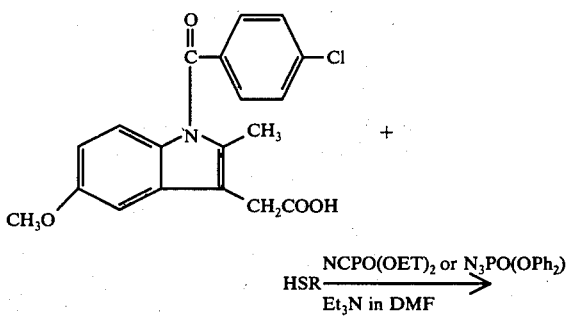

wherein R is defined as before.

SCHEME A

By way of illustration the 1-(p-chlorobenzoyl)-5-methoxy-2-methylindole-3-acetic acid is treated with an appropriate thiol and diethyl phosphorocyanidate or diphenyl phosphorazidate in the presence of triethylamine in dimethylformamide solution. This procedure is identical to the procedure which is described by Yamada et al., *J. Org. Chem.*, 39, 3302 (1974).

For instance 5.0 parts of 1-(p-chlorobenzoyl)-5-methoxy-2-methylindole-3-acetic acid is dissolved in 50 parts of dry N,N-dimethylformamide along with 2.3 parts of 4-tertbutylbenzenethiol, 3.8 parts of triethylamine and 2.8 parts of diethyl phosphorocyanidate and stirred for 3 hours. The reaction mixture is then diluted with benzene and washed with 5% aqueous citric acid. The benzene extracts are then treated with saturated aqueous sodium bicarbonate and dried over anhydrous sodium sulfate. Removal of the solvent under reduced pressure affords a residue. This residue is dissolved in ethanol, treated with darco and filtered. Diluting the filtrates with water, stirring and then cooling affords S-4-tert-butylphenyl 1-(4-chlorobenzoyl)-5-methoxy-2-methyl-3-indolethioacetate.

It would be obvious to those skilled in the art that the compounds of this invention in which R can be mono or polysubstituted phenyl are not necessarily limited to the phenyl substituents which have been exemplified but that other commonly employed phenyl substituents would also be within the range of this invention.

The compounds of formula I may be combined with various pharmaceutical carriers to provide compositions suitable for use as anti-inflammatory agents. The dosage of these compounds is dependent upon various factors, such as the compounds employed and the particular response obtained.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in degrees Centigrade (° C.) and relative amounts in parts by weight except as otherwise noted.

EXAMPLE 1

To a solution of 5.0 parts of 1-(p-chlorobenzoyl)-5-methoxy-2-methylindole-3-acetic acid in 50 parts of dry N,N-dimethylformamide are added with stirring and cooling 2.3 parts of 4-tert-butylbenzenethiol, 3.8 parts of triethylamine and then 2.8 parts of diethyl phosphorocyanidate. After the addition of the diethyl phosphorocyanidate is completed, the ice bath is removed and the mixture is stirred at ambient temperature for 3 hours. The reaction mixture is then diluted with benzene, and washed with 5% aqueous citric acid. The benzene extract is then treated with saturated aqueous sodium bicarbonate and dried over anhydrous sodium sulfate. Removal of the solvent under reduced pressure affords a residue. This residue is dissolved in ethanol, treated with darco and filtered. Diluting the filtrates with water, stirring and then cooling affords, as colorless crystals, S-4-tert-butylphenyl 1-(4-chlorobenzoyl)-5-methoxy-2-methyl-3-indolethioacetate. This compound melts at about 139°-140° C. and is represented by the following structural formula

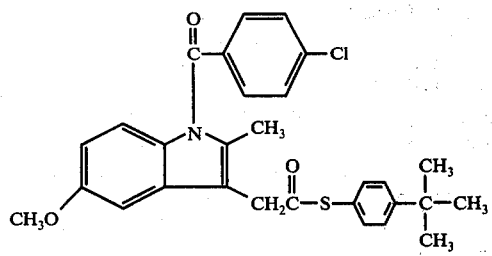

EXAMPLE 2

To a solution of 25 parts of 1-(p-chlorobenzoyl)-5-methoxy-2-methylindole-3-acetic acid in 150 parts of dry N,N-dimethylformamide are added under a nitrogen atmosphere, with stirring and cooling 7.7 parts of thiophenol, 7.77 parts of triethylamine and then 12.6 parts of diethyl phosphorocyanidate. After the addition of the diethyl phosphorocyanidate is completed, the reaction mixture is stirred for one hour. The ice bath is then removed and the mixture is stirred at ambient temperature for an additional hour. The reaction mixture is diluted with an equal volume of acetone; water is then carefully added until crystallization occurs.

Cooling of the reaction mixture gives crude yellow crystals. Recrystallization of this crude product from a mixture of acetone and water affords, as crystals, S-phenyl 1-(4-chlorobenzoyl)-5-methoxy-2-methyl-3-indolethioacetate. This compound melts at about 123°-124° C. and is represented by the following structural formula

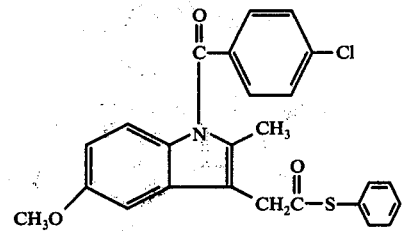

EXAMPLE 3

To a solution of 25 parts of 1-(p-chlorobenzoyl)-5-methoxy-2-methylindole-3-acetic acid in 200 parts of dry N,N-dimethylformamide are added 8.69 parts of p-toluenethiol, 7.77 parts of triethylamine and 12.56 parts of diethyl phosphorocyanidate with stirring under a nitrogen atmosphere in a bath which is maintained at −67° C. The resulting reaction mixture is stirred under the above-described conditions for 2 hours. After the 2 hour period a product crystallized out. This product is filtered off, washed with cold dimethylformamide and dried in vacuo to give crude crystals. Recrystallization of this material from hot acetone affords S-4-methylphenyl 1-(4-chlorobenzoyl)-5-methoxy-2-methyl-3-indolethioacetate. This compound melts at 134° C. and is represented by the following structural formula

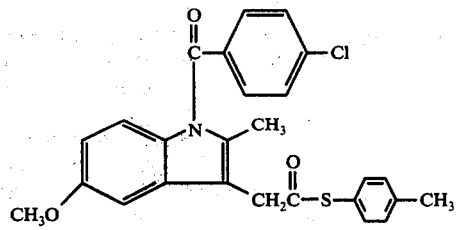

EXAMPLE 4

To a solution of 25 parts of 1-(p-chlorobenzoyl)-5-methoxy-2-methylindole-3-acetic acid in 200 parts of dry N,N-dimethylformamide are added 12.53 parts of 3,4-dichlorobenzenethiol 7.77 parts of triethylamine and 12.56 parts of diethyl phosphorocyanidate with stirring under a nitrogen atmosphere in a bath which is maintained at −67° C. The reaction mixture is stirred under the above-described conditions for 4 hours. The reaction mixture is then placed in a pan of cold water and stirred for an additional hour. This mixture is diluted with benzene and washed with 5% aqueous citric acid. The benzene extracts are then treated with saturated aqueous sodium bicarbonate and dried over anhydrous sodium sulfate. Removal of the solvent under reduced pressure affords a a yellow oil. This oil is dissolved in acetone and then cooled to induce crystallization. This procedure affords S-3,4-dichlorophenyl 1-(4-chlorobenzoyl)-5-methoxy-2-methyl-3-indolethioacetate. This compound melts at about 126°-127° C. and is represented by the following structural formula

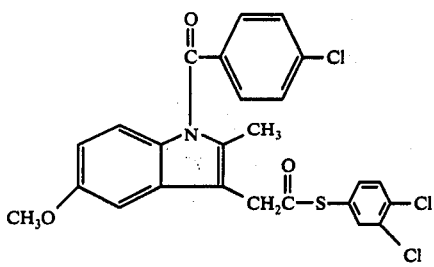

EXAMPLE 5

Substitution of p-nitrothiophenol for the 3,4-dichlorobenzenethiol of Example 4 and repetition of the procedure of Example 4 affords S-p-nitrophenyl 1-(4-chlorobenzoyl)-5-methoxy-2-methyl-3-indolethioacetate. This compound melts at about 160°–164° C. and is represented by the following structural formula

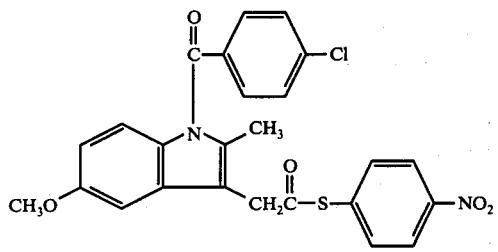

EXAMPLE 6

To a solution of 25 parts of 1-(p-chlorobenzoyl)-5-methoxy-2-methylindole-3-acetic acid in 150 parts of dry N,N-dimethylformamide are added with stirring and cooling at 0° C. under a nitrogen atmosphere 9.8 parts of p-methoxybenzenethiol, 7.77 parts of triethylamine and 12.56 parts of diethyl phosphorocyanidate. The reaction mixture is then stirred under the above-described conditions for 3 hours. The cold mixture is then diluted with methylene chloride, and washed with 5% aqueous citric acid. The methylene chloride layer is separated and washed with saturated aqueous sodium bicarbonate and then dried over sodium sulfate. Removal of the solvent under reduced pressure affords a crude oil. Crystallization of this oil from a mixture of acetone and water affords S-4-methoxyphenyl 1-(4-chlorobenzoyl)-5-methyl-3-indolethioacetate. This compound melts at about 126°–127° C. and is represented by the following structural formula

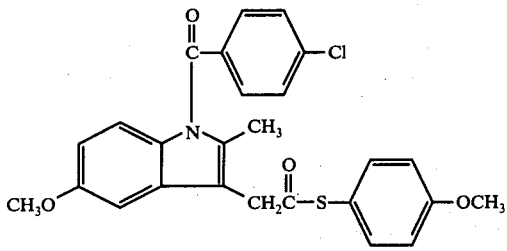

EXAMPLE 7

A mixture of 2.5 parts of 1-(p-chlorobenzoyl)-5-methoxy-2-methylindole-3-acetic acid, 150 parts of dry N,N-dimethylformamide, 8.76 parts of 4-aminothiophenol, 7.77 parts of triethylamine and 12.56 parts of diethyl phosphorocyanidate are stirred in an ice-bath under a nitrogen atmosphere for one hour. The ice bath is then removed and the reaction mixture is stirred at ambient temperature for an additional hour. The mixture is then diluted with ⅓ volume of acetone. Additional dilution of this mixture with water, stirring and cooling affords a crude product. Recrystallization of this crude product from ethanol gives S-4-aminophenyl 1-(4-chlorobenzoyl)-5-methoxy-2-methyl-3-indolethioacetate. This compound melts at about 137°–138° C. and is represented by the following structural formula

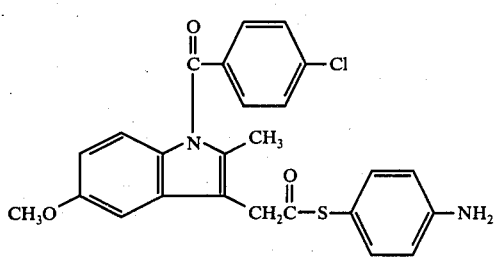

EXAMPLE 8

To a solution of 10.0 parts of 1-(p-chlorobenzoyl)-5-methoxy-2-methylindole-3-acetic acid in 50 parts of dry N,N-dimethylformamide are added with stirring and cooling 4.26 parts of 2,4,6 trimethylthiophenol, 5.66 parts of triethylamine and 9.14 parts of diethyl phosphorocyanidate. After the addition of the diethyl phosphorocyanidate is completed, the ice-bath is removed and the mixture is stirred at ambient temperature for 3 hours. The reaction mixture is then diluted with benzene and washed with 5% aqueous citric acid. The benzene extracts are then treated with saturated aqueous sodium bicarbonate and dried over anhydrous sodium sulfate. Removal of the solvents under reduced pressure affords a residue. This residue is dissolved in acetone, treated with darco and filtered. Diluting the filtrates with water affords, as crystals, S-2,4,6-trimethylphenyl 1-(4-chlorobenzoyl)-5-methoxy-2-methyl-3-indolethioacetate. This compound melts at about 135°–136° C. and is represented by the following structural formula

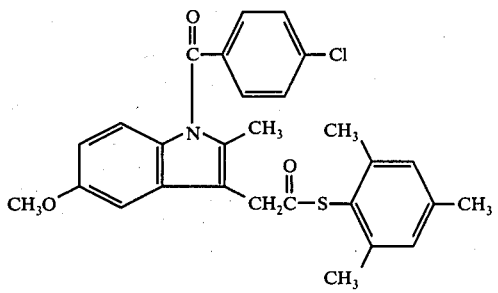

EXAMPLE 9

To a solution of 5.0 parts of 1-(p-chlorobenzoyl)-5-methoxy-2-methylindole-3-acetic acid in 75 parts of dry N,N-dimethylformamide are added with stirring and cooling, under a nitrogen atmosphere 3.85 parts of triphenylmethylthiol, 2.82 parts of triethylamine and 9.12 parts of diethyl phosphorocyanidate. The reaction mixture is stirred under the above-mentioned conditions for 1 hour. The cold reaction mixture is then diluted with benzene and washed with 5% aqueous citric acid. The benzene extracts are then treated with aqueous sodium bicarbonate, dried over anhydrous sodium sulfate and filtered. Removal of the solvent under reduced pressure affords an oil which is chromatographed on silica gel. Crystallization of the purified product from ethanol affords S-triphenylmethyl 1-(4-chlorobenzoyl)-5-methoxy-2-methyl-3-indolethioacetate. This compound melts at about 147°–148° C. and is represented by the following structural formula

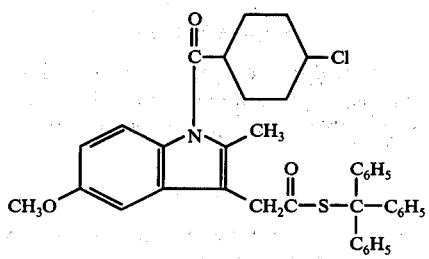

EXAMPLE 10

To a solution 25 parts of 1-(p-chlorobenzoyl)-5-methoxy-2-methylindole-3-acetic acid in 150 parts of dry N,N-dimethylformamide are added with stirring and cooling at 0° C. 814 parts of cyclohexylthiol, 14.15 parts of triethylamine and 22.8 parts of diethyl phosphorocyanidate. After the addition of the diethyl phosphorocyanidate is completed, the ice-bath is removed and the mixture is stirred at ambient temperature for 17 hours. The reaction mixture is then diluted with benzene and washed with 5% aqueous citric acid. The benzene extracts are then treated with saturated aqueous sodium bicarbonate and dried over anhydrous sodium sulfate. Removal of the solvent under reduced pressure affords a residue. This residue is then chromatographed on silica gel. Crystallization of the purified product from acetone: water affords S-cyclohexyl 1-(4-chlorobenzoyl)-5-methoxy-2-methyl-3-indolethioacetate. This compound melts at about 102°–104° C. and is represented by the following structural formula

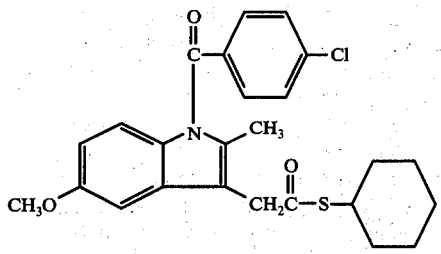

EXAMPLE 11

25 Parts of 1-(p-chlorobenzoyl)-5-methoxy-2-methylindole-3-acetic acid, 200 parts of dry N,N-dimethylformamide, 6.3 parts of 1-methyl-1-propanethiol, 7.77 parts of triethylamine and 12.56 parts of diethyl phosphorocyanidate are combined and stirred under a nitrogen atmosphere in a bath which is maintained at a temperature of −67° C. for 3 hours. After the 3 hour period, the bath is removed and the reaction mixture is allowed to reach cold-water temperature. This cold reaction mixture is then diluted with methylene chloride and washed with aqueous 5% citric acid. The benzene extracts are then treated with saturated aqueous sodium bicarbonate and dried over anhydrous sodium sulfate. Removal of the solvents under reduced pressure affords an oil. This oil is dissolved in benzene, washed several times with water and dried over anhydrous sodium sulfate. Removal of the solvent under reduced pressure affords a residue which is chromatographed on silica gel. Crystallization of the purified product affords S-(1-methyl-1-propyl)1-(4-chlorobenzoyl)-5-methoxy-2-methyl-3-indolethioacetate. This compound melts at about 78°–80° C. and is represented by the following structural formula

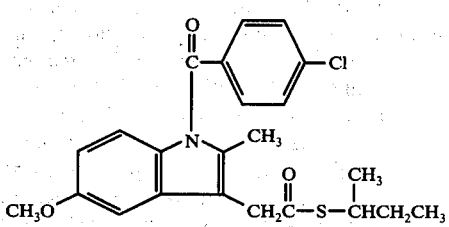

EXAMPLE 12

Substitution of 2-methyl-1-propanethiol for the 1-methyl-1-propanethiol of Example 11 and repetition of the procedure of Example 11 affords S-(2-methyl-1-propyl)1-(4-chlorobenzoyl)-5-methoxy-2-methyl-3-indolethioacetate. This compound melts at about 78°–80° C. and is represented by the following structural formula

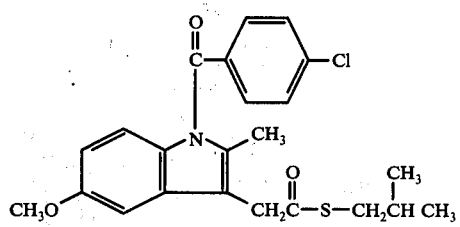

EXAMPLE 13

To a solution of 5.0 parts 1-(p-chlorobenzoyl)-5-methoxy-2-methylindole-3-acetic acid in 50 parts of dry N,N-dimethylformamide and 2.0 parts of 4-chlorobenzenethiol which is stirred under a nitrogen atmosphere and cooled in a bath which is maintained at −67° C. are added 1.55 parts of triethylamine and 2.5 parts of diethyl phosphorocyanidate. The resulting yellow solution is stirred for 4 hours. After the bath is removed, the reaction mixture is brought to a temperature above the freezing point of benzene. The mixture is then diluted with benzene and washed with 5% aqueous citric acid. The benzene extracts are then treated with saturated aqueous sodium bicarbonate solution and dried over anhydrous sodium sulfate. Removal of the solvent under reduced pressure affords an oil Crystallization of this oil from acetone and water affords S-4-chlorophenyl 1-(4-chlorobenzoyl)-5-methoxy-2-methyl-3-indolethioacetate. This compound melts at about 124°–126° C. and is represented by the following structural formula

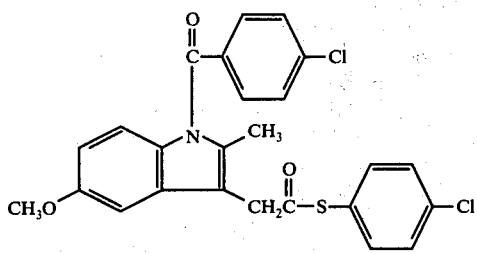

EXAMPLE 14

To a solution of 22.15 parts of 1-(p-chlorobenzoyl)-5-methoxy-2-methylindole-3-acetic acid in 200 parts of dry N,N-dimethylformamide and 10.1 parts of 2,5-dichlorobenzenethiol which is stirred under a nitrogen atmosphere and cooled in a bath which is maintained at −67° C. and added 7.77 parts of triethylamine and 12.5 parts of diethyl phosphorocyanidate. The resulting solution is then stirred for 3 hours. After the bath is removed the reaction mixture is brought to a temperature above the freezing point of benzene. The reaction mixture is then diluted with benzene and washed with 5% aqueous citric acid. The benzene extracts are then treated with saturated aqueous sodium bicarbonate solution and dried over anhydrous sodium sulfate. Removal of the solvent under reduced pressure affords an oil. Crystallization of this oil from hot acetone affords S-2,5-dichlorophenyl 1-(4-chlorobenzoyl)-5-methoxy-2-methyl-3-indolethioacetate. This compound melts at about 142° C. and is represented by the following structural formula

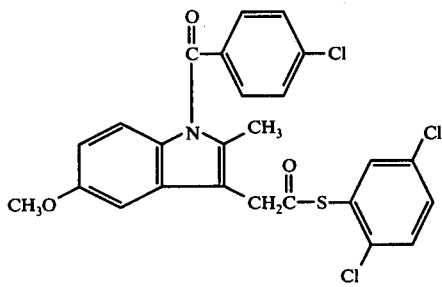

EXAMPLE 15

To a solution of 10.0 parts of 1-(p-chlorobenzoyl)-5-methoxy-2-methylindole-3-acetic acid in 50 parts of dry N,N-dimethylformamide are added with stirring and cooling 5.2 parts of α-toluenethiol, 8.5 parts of triethylamine and then 13.7 parts of diethyl phosphorocyanidate. After the addition of the diethyl phosphorocyanidate is completed, the ice-bath is removed and the mixture is stirred at ambient temperature for 3 hours. The reaction mixture is then diluted with benzene and washed with 5% aqueous citric acid. The benzene extracts are then treated with saturated aqueous sodium bicarbonate, and then dried over anhydrous sodium sulfate. Removal of the solvent under reduced pressure affords a residue. This residue is dissolved in acetone, treated with darco and filtered. Diluting the filtrates with water, stirring and cooling affords S-phenylmethyl 1-(4-chlorobenzoyl)-5-methoxy-2-methyl-3-indolethioacetate. This compound melts at about 105°-108° C. and is represented by the following structural formula

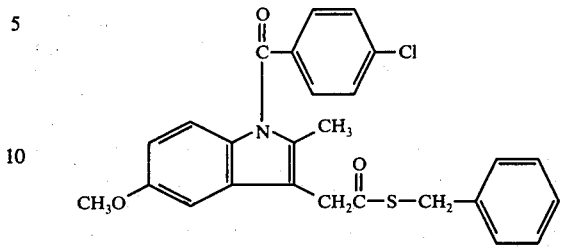

EXAMPLE 16

Pharmaceutical formulations are prepared in the following manner with amounts indicating the relative amounts per tablet, capsule, suppository or parenteral product.

Tablet 350 mgs. of a representative compound, e.g. S-4-tert-butylphenyl 1-(4-chlorobenzoyl)-5-methoxy-2-methyl-3-indolethioacetate are dissolved in isopropyl alcohol and distributed on 223 mgs. of lactose. The mixture is air-dried and passed through a 40 mesh screen. 150 mgs. of corn starch and 23 mgs. of polyvinylpyrrolidone are added to the drug substance lactose mixture, mixed thoroughly and passed through a 40 mesh screen. The mixture is then granulated with isopropyl alcohol, spread on trays, and dried at 120° F. for 16 hours. The dried granulation is then screened. The granules are mixed thoroughly with 4 mgs. of magnesium stearate and the mixture compressed into tablets of the appropriate size. There is thus obtained a tablet having a concentration of active ingredient of 350 mgs.

Capsule 350 mgs. of S-4-tertbutylphenyl 1-(4-chlorobenzoyl)-5-methoxy-2-methyl-3-indolethioacetate are mixed thoroughly with 181 mgs. of corn starch and 181 mgs. of lactose, screened through a 40 mesh screen, and remixed. 38 mgs. of talc are added and the mixture is thoroughly mixed and filled into the appropriate hard gelatin capsule by hand or machine using 750 mgs. fill per capsule. There is thus obtained a capsule having a concentration of active ingredients of 350 mgs.

In the preparation of tablets and capsules from the compounds of the present invention, a variety of excipients can be used. These are summarized as follows: Sugars such as lactose, sucrose, mannitol, or sorbitol; starches such as corn starch, tapioca starch, or potato starch; cellulose derivatives such as sodium carboxymethyl cellulose, ethyl cellulose, or methyl cellulose; gelatin; calcium phosphates such as dicalcium phosphate or tricalcium phosphate; sodium sulfate; calcium sulfate; polyvinylpyrrolidone; polyvinyl alcohol; stearic acid; alkaline earth metal stearates such as magnesium stearate; stearic acid vegetable oils such as peanut oil, cottonseed oil, sesame oil, olive oil, corn oil, surfactants (nonionic, cationic, anionic); ethylene glycol polymers; beta-cyclodextrin; fatty alcohols; hydrolyzed cereal solids; as well as other non-toxic compatible fillers, binders, disintegrants, and lubricants commonly used in pharmaceutical formulations.

Parenteral Products 35 mgs. of S-4-tertbutylphenyl 1-(4-chlorobenzoyl)-5-methoxy-2-methyl-3-indolethioacetate are dissolved in 0.5 ml of ethanol and 5.0 ml of sesame oil, filtered and filled into an ampul and sealed. The ampul is then sterilized by an appropriate procedure. There is thus obtained an ampul having a concentration of active ingredient 35 mg/5ml.

In the preparation of parenteral products from the compounds of the present invention a variety of vehicles and solubilizers can be used. These are summarized as follows: Vegetable oils such as peanut, corn, cottonseed, sesame oil, benzyl alcohol, saline, phosphate buffer, water, ethylene glycol polymers, urea, dimethylacetamide, triton, dioxolanes, ethyl carbonate, ethyl lactate, glycerol formal, isopropyl myristate, surfactants (nonionic, cationic, anionic), polyalcohols, ethanol.

Suppository 650 mgs. of cocoa butter are melted, preferably on a water or steam bath to avoid local overheating, then 350 mgs. of S-4-tertbutylphenyl 1-(4-chlorobenzoyl)-5-methoxy-2-methyl-3-indolethioacetate is either emulsified or suspended in the melt. Finally, the mass is poured into cooled metal molds, which are chrome plated and the suppository is readily solidified. The total weight of the suppository is 1000 mg.

In the preparation of suppositories from the compounds of the present invention a variety of vehicles and bases for suppository application can be used. These are summarized as follows: Triglycerides of oleic, palmitric, and stearic acids (cocoa butter), partially hydrogenated cottonseed oil, branched saturated fatty alcohols such as Suppository base G, Hydrogenated coconut oil triglycerides of $C_{12}$-$C_{18}$ fatty acids, water dispersible vehicles such as the polyethylene glycols, glycerin, gelatin, polyoxyl 40 stearates, and polyethylene-4-sorbitan monostearates, and materials which can raise the melting point of the suppository base, such as beeswax, spermaceti, etc.

What I claim is:

1. A compound of the formula wherein R is

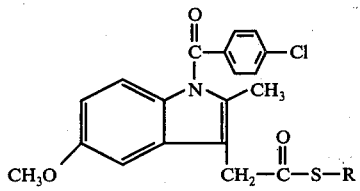

cycloalkyl radical containing 3 to 6 carbon atoms which can be optionally substituted by an alkyl radical containing 1 to 9 carbon atoms or halo; phenyl, monosubstituted or polysubstituted phenyl wherein the substituent can be linear or branched chain alkyl radical containing 1 to 9 carbon atoms, halo, alkoxy wherein the alkyl radical contains 1 to 9 carbon atoms, amino or nitro and may be alike or different.

2. As in claim 1, a compound of the formula wherein R is

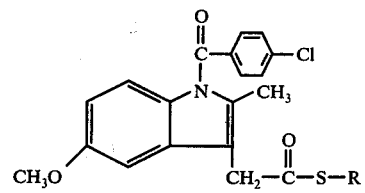

a cycloalkyl radical containing 3 to 6 carbon atoms which can be optionally substituted by an alkyl radical containing 1 to 9 carbon atoms or halo.

3. As in claim 1, a compound of the formula

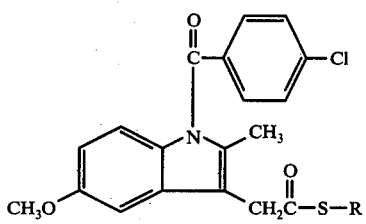

wherein R is phenyl, monosubstituted or polysubstituted phenyl wherein the substituent can be linear or branched chain alkyl radical containing 1 to 9 carbon atoms, halo, alkoxy wherein the alkyl radical contains 1 to 9 carbon atoms, amino, or nitro, and may be alike or different.

4. As in claim 1, the compound which is S-4-tertbutylphenyl 1-(4-chlorobenzoyl)-5-methoxy-2-methyl-3-indolethioacetate.

5. As in claim 1, the compound which is S-2,4,6-trimethylphenyl 1-(4-chlorobenzoyl)-5-methoxy-2-methyl-3-indolethioacetate.

6. As in claim 1, the compound which is S-cyclohexyl 1-(4-chlorobenzoyl)-5-methoxy-2-methyl-3-indolethioacetate.

7. As in claim 1, the compound which is S-phenyl 1-(4-chlorobenzoyl)-5-methoxy-2-methyl-3-indole-thioacetate.

8. As in claim 1, the compound which is S-4-aminophenyl 1-(4-chlorobenzoyl)-5-methoxy-2-methyl-3-indolethioacetate.

9. As in claim 1, the compound which is S-4-chlorophenyl 1-(4-chlorobenzoyl)-5-methoxy-2-methyl-3-indolethioacetate.

10. As in claim 1, the compound which is S-4-methoxyphenyl 1-(4-chlorobenzoyl)-5-methoxy-2-methyl-3-indolethioacetate.

11. As in claim 1, the compound which is S-3,4-dichlorophenyl 1-(4-chlorobenzoyl)-5-methoxy-2-methyl-3-indolethioacetate.

12. As in claim 1, the compound which is S-4-nitrophenyl 1-(4-chlorobenzoyl)-5-methoxy-2-methyl-3-indolethioacetate.

13. As in claim 1, the compound which is S-4-methylphenyl 1-(4-chlorobenzoyl)-5-methoxy-2-methyl-3-indolethioacetate.

14. As in claim 1, the compound which is S-2,5-dichlorophenyl 1-(4-chlorobenzoyl)-5-methoxy-2-methyl-3-indolethioacetate.

* * * * *